US00PP22669P2

(12) United States Plant Patent
Denis

(10) Patent No.: US PP22,669 P2
(45) Date of Patent: Apr. 17, 2012

(54) ***CALATHEA* PLANT NAMED 'COBRA PINK'**

(50) Latin Name: ***Calathea* hybrid**
Varietal Denomination: Cobra Pink

(76) Inventor: Rene Denis, Beervelde (BE)

( * ) Notice: Subject to any disclaimer, the term of this patent is extended or adjusted under 35 U.S.C. 154(b) by 0 days.

(21) Appl. No.: 12/925,044

(22) Filed: Oct. 12, 2010

(51) Int. Cl.
*A01H 5/00* (2006.01)

(52) U.S. Cl. ..... Plt./375

(58) Field of Classification Search ..... Plt./375
See application file for complete search history.

(56) References Cited

OTHER PUBLICATIONS

GTITM UPOVROM Citation for 'Cobra Pink' as per QZ PBR 20081045; May 13, 2008.*

* cited by examiner

*Primary Examiner* — Kent L Bell
(74) *Attorney, Agent, or Firm* — Cassandra Bright

(57) ABSTRACT

A new and distinct *Calathea* cultivar named 'COBRA PINK' is disclosed, characterized by distinctive green-white flowers tinged with pink, a compact, sturdy and long peduncles. The new variety is a *Calathea,* normally produced as an indoor ornamental plant.

1 Drawing Sheet

Figure 1:
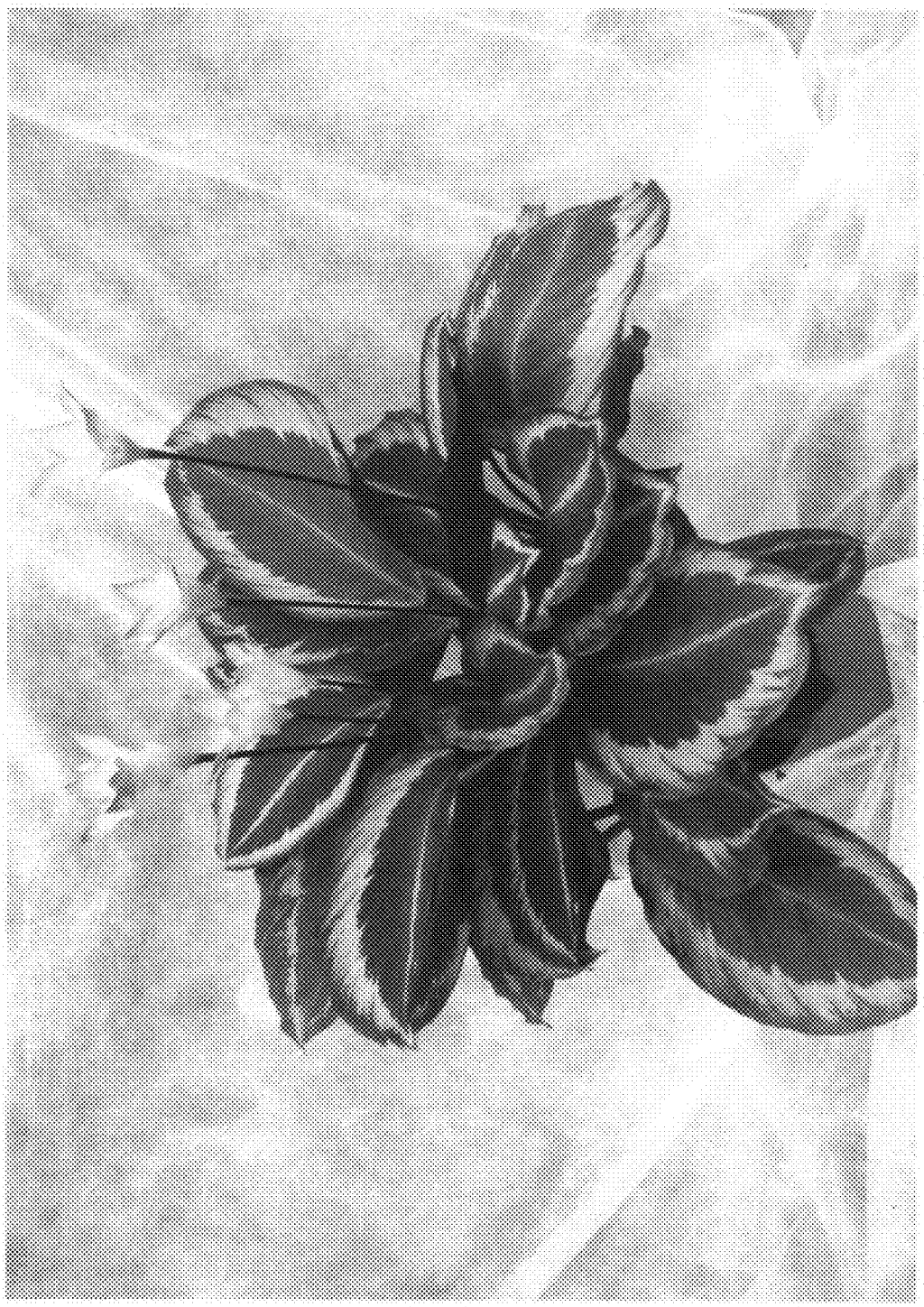

Latin name of the genus and species: *Calathea* hybrid.
Variety denomination: 'COBRA PINK'.

BACKGROUND OF THE INVENTION

The new cultivar was discovered as a result of a planned breeding program directed by the inventor, Rene Denis a citizen of Belgium. The seed parent is an undistributed, unpatented proprietary variety *Calathea* hybrid 'Z204' and the pollen parent is the undistributed, unpatented proprietary variety *Calathea* hybrid 'Z154.' The cross resulting in 'Cobra Pink' was made in November 2004, the new variety was discovered as a seedling in March 2005, by the inventor in a commercial research greenhouse in Beervelde, Belgium.

Asexual reproduction of the new cultivar 'COBRA PINK' was first performed in December 2008, by tissue culture at a commercial laboratory in Brussels, Belgium. Multiple generations have since been produced and have shown that the unique features of this cultivar are stable and reproduced true to type in successive generations.

SUMMARY OF THE INVENTION

The cultivar 'COBRA PINK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COBRA PINK' These characteristics in combination distinguish 'COBRA PINK' as a new and distinct *Calathea* cultivar:

1. Sturdy plant with a compact habit
2. Green-White colored flower with pink margins
3. Long peduncles.
4. Broad dark green leaves with grey-green margins and veins.

PARENT COMPARISON

Plants of the new cultivar 'COBRA PINK' are similar to plants of the seed parent, *Calathea* hybrid 'Z204' in most horticultural characteristics, however, plants of the new cultivar 'COBRA PINK' are slower growing with shorter leaves and longer peduncles. Additionally, plants of 'COBRA PINK' have foliage which is greyed-green along the margins and veins, whereas 'Z204' has solid green foliage with a small white coloration along the main vein Plants of the new cultivar 'COBRA PINK' are similar to plants of the pollen parent, *Calathea* hybrid 'Z154' in most horticultural characteristics, however, plants of the new cultivar 'COBRA PINK' grow faster than 'Z154' and produce longer leaves. Additionally, plants of 'COBRA PINK' produce white-green flowers with a pink tinge, whereas 'Z154' produces green flowers on a shorter peduncle.

COMMERCIAL COMPARISON

'COBRA PINK' can be compared to the commercial variety *Calathea hybrida* 'Mia' U.S. Plant Pat. No. 16,425. The two varieties are similar in many horticultural characteristics, however, plants of 'COBRA PINK' differ in producing longer peduncles and different color flowers. Additionally, plants of 'COBRA PINK' are larger and grow faster than plants of 'Mia.'

BRIEF DESCRIPTION OF THE PHOTOGRAPH

The accompanying photograph in FIG. 1 illustrates in full color a typical plant of 'COBRA PINK' grown in a commercial greenhouse in Beervelde, Belgium in a 17 cm container. Age of the plant photographed is approximately 45 weeks from a rooted plantlet. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used.

The following observations and measurements describe 'COBRA PINK' plants grown in a commercial greenhouse in Beervelde, Belgium. The growing temperature ranged from 21° C. to 26° C. daytime and 20° to 23° C. at night. No growth regulators or other chemical treatments were used. Measurements and numerical values represent averages of typical plant types.

Botanical classification: *Calathea* hybrid 'COBRA PINK.'

PROPAGATION

Time to initiate roots: Summer: 12 to 16 days at approximately 22° C. Winter: 19 to 23 days at approximately 23° C.

Root description: Non-fleshy, moderately fibrous, densely branched, colored near RHS Grey-Brown 199D Rhizomes: Not present.

Propagation method: Tissue culture.

PLANT

Age of plant described: 45 weeks from a rooted plantlet.

Growth habit: Broad obovate, top flattened

Pot size of plant described: 17 cm

Height: Average: 52.7 cm.

Plant spread: Average: 54.3 cm.

Growth rate: Moderate

Main stem color: Near RHS Greyed-Purple 187A

Main stem texture: Smooth

Branching characteristics: Main stems grow directly from the base, no lateral branches Length of branches: Average 6.1 cm.

Quantity of branches: Average: 7

Characteristics of branches: Form: Elliptic in cross section.

*Diameter.*—Average diameter at widest: 1.1 cm, average width at narrowest: 8 mm.

*Color.*—Near RHS Greyed-Purple 187A.

*Texture.*—Smooth.

*Strength.*—Strong.

Internode length: Average: 0.2 cm.

FOLIAGE

Leaf:

*Arrangement.*—Alternate, distichous.

*Quantity.*—Approximately 4 per main stem.

*Average length.*—20.6 cm (excluding petiole).

*Average width.*—12.2 cm.

*Shape of blade.*—Broad elliptic to broad obovate.

*Apex.*—Abruptly acute.

*Base.*—Rounded.

*Margin.*—Entire, moderately wavy.

*Texture of top surface.*—Smooth, glossy.

*Pubescence.*—No leaf pubescence.

*Aspect.*—Lower leaves slightly drooping in an average angle of −25° (0°=horizontal); leaves in mid-section of plant leaves horizontal; upper leaves slightly upright in an average angle of 50° (0°=horizontal).

*Color.*—Young foliage upper side: Near RHS Green 137A, blotched along the main vein; near Green 143A, margins Near Grey-Green 191B and 194B, both colors present individually, outermost edge of margin near Green N137A. Young foliage under side: Near RHS Greyed-Purple N186C, margins slightly lighter; N186C. Mature foliage upper side: Near RHS Green N137A blotched lighter along the main vein; near Green 143A, margins colored near Greyed-Green 191B and 191C, both colors present, outermost edge of margin near Green; N137A. Mature foliage under side: Near RHS N186B, margins; N186C.

*Venation.*—Type: Pinnate. Venation color upper side: Near RHS Green 138B (main vein), secondary veins near Green 139A. Venation color under side: Near RHS Greyed-Green 197B.

*Petiole.*—Length: Average 25.3 cm (excl. geniculum). Diameter: Petiole shaped elliptic in diameter, average width at widest: 0.5 cm, average width at narrowest: 0.4 cm. Main Stem Color: Near RHS Greyed-Purple 187A. Main Stem Texture: Smooth. Main stem length: Approximately 40 cm.

*Petiole sheath.*—Present: Yes. Length: Average: 12.7 cm. Diameter: Average: 0.8 cm. Color: Near RHS Greyed-Purple 183B.

*Cataphylls.*—Present: Not present.

*Geniculum.*—Shape: Rounded. Texture: Smooth. Length: Average: 3.1 cm. Diameter: Average: 0.45 cm. Color: Near RHS Greyed-Orange 177A. Other Features: No.

FLOWER

Days to flowering from rooted plantlet: 40 weeks

Natural flowering season: Late spring and early summer.

Inflorescence and flower type and habit: Inflorescence upright, consisting of an average of 7 bracts with small, obscured individual flowers in between bracts. Bracts shaped ovate, average length: 4.2 cm, average width: 2.1 cm, colored near Green-White 157D. Apex of bract tinged near Greyed Purple 186C. Bract arrangement: Whorled. Bract apex: Acute. Bract base: Attenuate. Bract margin: Entire. Bract coloration upper surface: colored near Green-White 157D. Apex of bract tinged near Greyed-Purple 186C.

Rate of flower opening: 20 to 30 days from bud to fully opened flower.

Flower longevity on plant: Average: 15 days.

Quantity of buds and flowers per plant: Average: 4 inflorescences, with approximately 1 flower bud and 3 flowers.

Persistent or self-cleaning: Persistent

Bud:

*Shape.*—Lanceolate.

*Length.*—7.3 cm.

*Diameter.*—1.5 cm.

*Color.*—Base near RHS Yellow 4D, mid-section Green White 157D, top Greyed-Green 191C with flush near Greyed-Purple 186C.

Individual flower:

*Diameter.*—Approximately 2.3 cm.

*Depth.*—Approximately 2.1 cm.

Inflorescence:

*Diameter.*—Inflorescence: 6.2 cm.

*Depth.*—Inflorescence: 6.6 cm.

Flower shape: Cupped.

Petals:

*Quantity.*—1.

*Arrangement.*—A single petal is present at the back of each individual flower.

*Length.*—2.5 cm.

*Width.*—2.4 cm.

*Shape.*—Obcordate.

*Apex.*—Emarginate.

*Base.*—Cuneate.
*Margin.*—Entire.
*Texture, upper and lower surfaces.*—Both sides smooth, upper surface glossy, lower surface dull. Color: When opening, upper surface: Near RHS Yellow-Green 149D, top near Green-White 157D base tinged Red 37D. When opening, lower surface: RHS Yellow-Green 149D, top near Green-White 157D base tinged Red 37C. Fully opened, upper surface: Near RHS Yellow-Green149D, top 157D base tinged Red 37C. Fully opened, lower surface: Near RHS Yellow-Green 149D, top Green-White 157D base tinged Red 37C.

Staminoides: No staminoides present

Sepals: No sepals present

Peduncles:
*Length.*—Approximately 33.4 cm.
*Diameter.*—0.4 cm.
*Angle.*—About 0° to the lateral branch (0=vertical).
*Strength.*—Moderately strong.
*Texture.*—Smooth, moderately glossy.
*Color.*—Near RHS Greyed-Purple 183B.

Fragrance: No fragrance

REPRODUCTIVE ORGANS

Stamens:
*Number.*—Average: 2.

Anthers: Shape: Oblong. Length: Approximately 0.2 cm. Color: RHS 155A Pollen: Color: RHS 155D. Quantity: low.

Pistil:
*Number.*—1.
*Length.*—0.3 cm.
*Style.*—Length: 0.1 cm. Color: RHS 155A.
*Stigma.*—Shape: acute. Color: RHS 155A. Ovary Color: RHS 155A.

OTHER CHARACTERISTICS

Seeds and fruits: Not observed to date.

Disease/pest resistance: Neither resistance nor susceptibility to pathogens and pests common to *Calathea* have been observed.

Temperature tolerance: The new variety tolerates temperatures between 19 to 30° C.

What is claimed is:

1. A new and distinct cultivar of *Calathea* plant named 'COBRA PINK' as herein illustrated and described.

* * * * *